United States Patent [19]

Thompson et al.

[11] Patent Number: 4,517,840

[45] Date of Patent: May 21, 1985

[54] ULTRASONIC SECTOR SCANNER HAVING FLUID REPLACEMENT CAPABILITY

[75] Inventors: Craig R. Thompson, Rancho Cordova; Ronald C. Carnes, Folsom; Ted F. Naumann, Jr., Shingle Springs, all of Calif.

[73] Assignee: General Electric Company, Milwaukee, Wis.

[21] Appl. No.: 667,397

[22] Filed: Nov. 2, 1984

Related U.S. Application Data

[63] Continuation of Ser. No. 434,826, Oct. 18, 1982, abandoned.

[51] Int. Cl.³ .............................................. G01N 29/04
[52] U.S. Cl. ........................................ 73/644; 73/634; 128/660
[58] Field of Search ................... 73/644, 639; 128/660

[56] References Cited

U.S. PATENT DOCUMENTS

| | | | |
|---|---|---|---|
| 4,149,419 | 4/1979 | Connell et al. | 73/644 |
| 4,165,648 | 8/1979 | Pagano | 73/639 |
| 4,237,901 | 12/1980 | Taenzer | 73/644 |
| 4,316,271 | 2/1982 | Evert | 73/644 |

Primary Examiner—A. V. Ciarlante
Attorney, Agent, or Firm—Flehr, Hohbach, Test, Albritton & Herbert

[57] ABSTRACT

A sector scanner which compensates for fluid leakage from the sealed transducer cavity includes a bladder in the cavity which is vented to the outside atmosphere whereby the bladder expands to compensate for the loss of fluid and a differential pressure between the cavity and the outside atmosphere is avoided. Alternatively, a fluid filled bladder is provided outside of the cavity and a port in the bladder is in fluid communication with the sealed cavity whereby fluid lost from the cavity is replaced by the fluid filled bladder. The bladder can be expandible with the fluid therein being under pressure.

3 Claims, 3 Drawing Figures

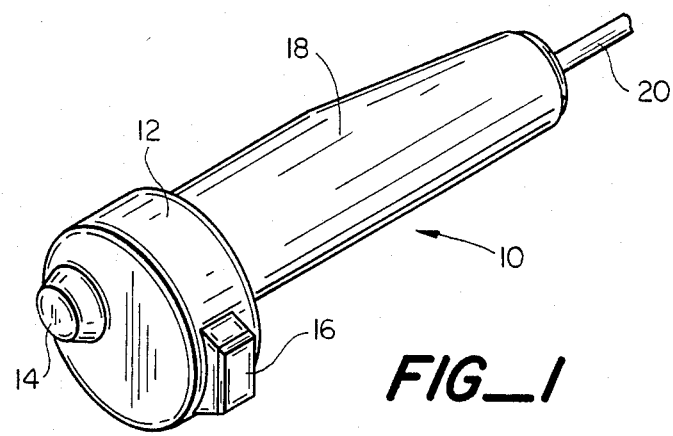
FIG_1
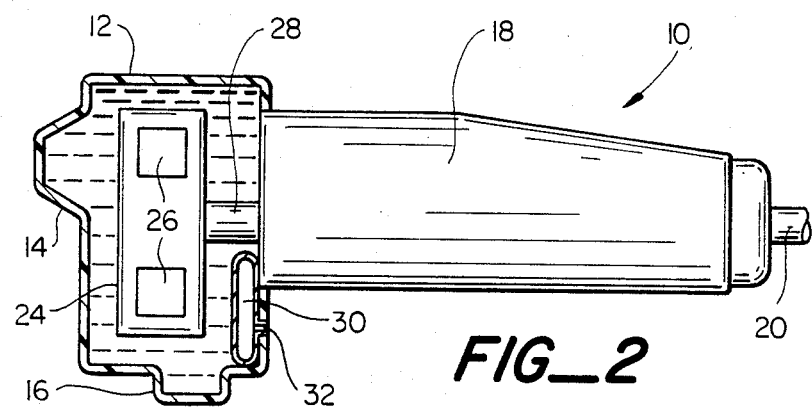
FIG_2
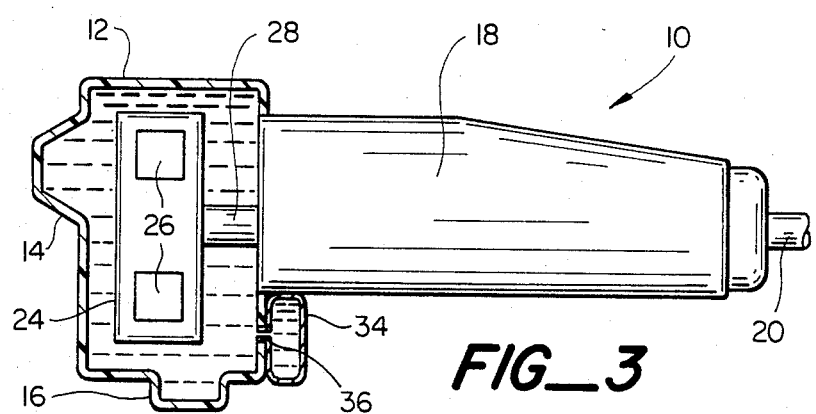
FIG_3

ULTRASONIC SECTOR SCANNER HAVING FLUID REPLACEMENT CAPABILITY

This is a continuation of application Ser. No. 434,826 filed 10/18/82, now abandoned.

This invention relates to handheld ultrasonic scanners such as used for medical diagnostic purposes.

Ultrasonic diagnostic systems are known and commercially available for medical diagnostic purposes. Briefly, such systems utilize sound transducers to transmit ultrasonic waves (e.g. on the order of several megahertz) into a patient and to receive echo signals. In one mode of operation a handheld transducer array is used for transmission and reception of ultrasonic signals. The echo signals are applied to a time gain compensated amplifier to adjust the echo signals for attenuation in passing through the patient. The adjusted signals are then passed through an analog to digital conversion and video processing circuitry and thence to scan converter circuitry for display formatting.

A handheld sector scanner is disclosed in copending application Ser. No. 290,838 filed Aug. 7, 1981 now U.S. Pat. No. 4,453,409 for "Ultrasonic Sector Scanner Utilizing Rotating Transducers". The disclosed ultrasonic sector scanner includes a housing, a shaft rotatably mounted in the housing, and a motor mounted within the housing and coupled to rotate the shaft. A transducer wheel, coupled to the shaft for rotating a plurality of transducers, is positioned in a sealed cavity in one end of the housing for directing ultrasonic energy through ports to a patient and for receiving echo signals from the patient.

Transmission and reception of the ultrasound requires that the acoustic paths between the transducers and the ports be a liquid. Thus, the sealed end of the housing in which the transducers are located is liquid filled. However, liquid losses from the sealed cavity occur as a result of fluid migration through the plastic housings. As a result of the liquid loss a pressure differential develops across the sealed housing joints and tends to pull air into the cavity and in the acoustic path between the transducers and ports. Ingested air causes a dramatic degradation of the sector scanner image performance.

An object of the present invention is an improved sector scanner for use in a medical diagnostic system.

Another object of the invention is a sector scanner having a fluid filled cavity in which air entry is prevented.

In accordance with one feature of the invention a pliable and impermeable bladder is cooperatively arranged with the fluid filled cavity to prevent air entry therein.

In one embodiment, the bladder is positioned within the fluid filled cavity and has a port which is connected to the ambient atmosphere. Thus, as fluid escapes from the cavity, air enters the bladder and prevents a pressure differential from developing between the cavity and the external atmosphere. The bladder expands to occupy the space from which the fluid escapes.

In another embodiment, an expandable bladder is positioned outside of the cavity and has a port which is connected to the cavity. The bladder is filled with the same fluid which is in the cavity, and any fluid which escapes from the cavity is replaced by fluid from the bladder.

The invention and objects and features thereof will be more readily apparent from the following detailed description and appended claims when taken with the drawing, in which:

FIG. 1 is a perspective view of an ultrasonic sector scanner.

FIG. 2 is a side view partially in section illustrating the sector scanner of FIG. 1 in accordance with one embodiment of the present invention.

FIG. 3 is a side view partially in section illustrating the sector scanner of FIG. 1 in accordance with another embodiment of the invention.

Referring now to the drawings, FIG. 1 is a perspective view of an ultrasonic sector scanner which includes a housing shown generally at 10 of suitable configuration for manual support by an operator. The housing 10 is enlarged at one end portion and defines a sealed cavity 12 which accommodates a rotating transducer assembly. Ports 14 and 16 provide for the transmission of ultrasonic energy from the transducers within the sealed cavity 12 and a patient undergoing examination. Signals received by the transducers are passed through internal electronics within the handle portion 18 and through cable 20 to external computer means (not shown) for processing and display. Mounted within handle portion 18 of the housing 10 is a motor and drive shaft which extends into the filled cavity 12 by rotating the transducers.

As above described, the sealed cavity 12 is filled with a fluid to facilitate the flow of ultrasonic energy between the transducers and the ports of the scanner. It has been discovered that over a period of time the fluid will escape from the sealed cavity either through seals in the housing structure or through the housing body, particularly when the housing is made of a plastic material. The loss of fluid creates a differential pressure between the sealed cavity and the ambient atmosphere which results in the entry of air into the sealed cavity. The presence of the air has a degrading effect on the operation of the sector scanner and the electrical signals generated thereby.

In accordance with the present invention a pliable and impermeable bladder is cooperatively arranged with the fluid filled cavity to prevent air entry into the cavity as a result of loss of fluid. FIG. 2 is a side view partially in section of the sector scanner of FIG. 1 in accordance with one embodiment of the invention. The end portion defining the sealed cavity 12 is shown in section, and mounted therein is the transducer assembly 24 including the transducers 26 which is rotatably mounted on shaft 28. To facilitate illustration of the invention, mirrors are not shown which are normally positioned within the cavity to direct the ultrasonic energy between the transducers 26 and the ports 14 and 16.

Mounted within the fluid filled cavity 12 in the end portion is a pliable and impermeable bladder 30 made of rubber, for example, which has a port 32 extending through the housing wall to the outside atmosphere. When the cavity 12 is initially filled with fluid, the bladder 30 is deflated. Since the bladder 32 is vented to the outside atmosphere, any space due to leakage of the fluid from the cavity 12 will be replaced by inflation of the bladder 30. Thus, space within the cavity previously occupied by the escaping fluid is occupied by the inflating bladder rather than by air entering the cavity. Accordingly, no differential pressure is established between the cavity and the outside atmosphere.

FIG. 3 is a side view of the sector scanner of FIG. 1 with end portion defining cavity 12 in section which illustrates another embodiment of the invention. In this embodiment an expandable bladder 34 is provided outside of the housing and includes a port 36 which passes through the wall of the housing 10 in communication with the cavity. In this embodiment when the cavity is initially filled with fluid, the bladder 34 is also filled with the fluid. Thereafter, any fluid which escapes from the cavity is replaced by the fluid in the bladder 34, and the bladder 34 contracts as the fluid passes therefrom into the cavity 12. The bladder can be expandible, and the fluid in the bladder can then be under pressure.

The use of a pliable impermeable bladder to compensate for fluid escaping from the sealed cavity maintains the optimum ultrasonic transmission characteristics of the sector scanner, and the images obtained using signals therefrom do not deteriorate as fluid escapes from the cavity. While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A hand-held scanner for use in ultrasonic medical diagnostic systems comprising
   a housing having a sealed end portion,
   a shaft rotatably mounted in said housing,
   a motor mounted within said housing and coupled to rotate said shaft,
   a transducer assembly coupled to said shaft and positioned in said sealed end portion,
   a fluid in said sealed end portion and displacing essentially all air therefrom, and
   a pliable, impermeable bladder means cooperatively arranged with said sealed end portion to automatically prevent air from entering said sealed end portion as a consequence of fluid escaping from said sealed end portion, said bladder means being positioned within said sealed end portion and vented to the outside atmosphere.

2. A scanner as defined by claim 1 wherein said scanner is a sector scanner.

3. In a hand-held scanner having ultrasonic transducer means positioned within a liquid filled, sealed cavity, means for automatically compensating for fluid escaping from said sealed cavity comprising a pliable, impermeable bladder means cooperatively arranged with said sealed cavity to prevent air from entering said sealed cavity as a consequence of fluid escaping from said sealed cavity, said bladder means being positioned within said sealed cavity and vented to the outside atmosphere.

* * * * *